United States Patent [19]

Loge et al.

[11] Patent Number: 4,973,116
[45] Date of Patent: Nov. 27, 1990

[54] ROD-SHAPED LIGHT CONDUCTOR FOR MEDICAL PURPOSES

[75] Inventors: Hans Loge, Biberach; Bernhard Kuhn, Schemmerhofen, both of Fed. Rep. of Germany

[73] Assignee: Kaltenbach & Voight GmbH & Co., Biberach an der Riss, Fed. Rep. of Germany

[21] Appl. No.: 873,395

[22] Filed: Jun. 12, 1986

[30] Foreign Application Priority Data

Jun. 28, 1985 [DE] Fed. Rep. of Germany ....... 3523286

[51] Int. Cl.$^5$ ................................................ G02B 6/00
[52] U.S. Cl. ............................ 350/96.10; 350/96.24; 427/163; 427/167
[58] Field of Search ............... 350/96.10, 96.23, 96.24, 350/96.29, 96.30, 96.34; 427/163, 165, 167

[56] References Cited

U.S. PATENT DOCUMENTS

| | | | |
|---|---|---|---|
| 3,563,716 | 2/1971 | Li | 350/96.24 X |
| 3,659,915 | 5/1972 | Mauver et al. | 350/96.30 |
| 3,966,300 | 6/1976 | Bernsee | 350/96.34 |
| 3,986,854 | 10/1976 | Serivo et al. | 350/96.1 X |
| 4,287,224 | 9/1981 | Heimbach et al. | 427/167 X |
| 4,317,615 | 3/1982 | Herold | 350/96.1 X |
| 4,437,727 | 3/1984 | Treber | 350/96.30 |
| 4,504,113 | 3/1985 | Baak | 350/96.34 X |
| 4,540,601 | 9/1985 | Nath | 427/163 |
| 4,573,761 | 3/1986 | McLachlan et al. | 350/96.1 X |

Primary Examiner—John D. Lee
Attorney, Agent, or Firm—Scully, Scott, Murphy & Presser

[57] ABSTRACT

A rod-shaped light conductor for medical purposes, for example, which is employed in the dental medicine. The light conductor is protected against thermal stresses through the intermediary of a special surface coating, as a result of which there is prevented any deterioration in the discharge of light from the end surfaces of the light conductor.

4 Claims, 1 Drawing Sheet

ROD-SHAPED LIGHT CONDUCTOR FOR MEDICAL PURPOSES

BACKGROUND OF THE INVENTION

1. Field of the Invention

The present invention relates to a rod-shaped light conductor for medical purposes which, for example, are employed in the dental medicine.

2. Discussion of the Prior Art

A light conductor of this type which is built into a dental handpiece has become known in the technology, for instance, from the disclosure of German Laid-Open Patent Appln. No. 33 32 628.

Handpieces of that type, or in effect, such kinds of light conductors subsequent to disassembling thereof, as in general all light conductors which are utilized in the medical technology, must be cleaned or sterilized from time to time, in essence, repeatedly cleaned. In this instance, the light conductor is consequently subjected to thermal stresses, for example, during sterilizing thereof in an autoclave at a temperature of 134° C., and during washing in an automatic washer exposed to a socalled disinfector at a temperature of 98° C. As a consequence of these thermal stresses, the light conductors are increasingly attacked or corroded about their outer surface so as to become dulled and their light-transmissiveness is continually decreased, as a result of which the desired exit of light from the end surface or surfaces of the light conductor will increasingly deteriorate.

SUMMARY OF THE INVENTION

The present invention, as described in detail hereinbelow, accordingly has as its object to alleviate the foregoing disadvantages by providing a light conductor of the above-mentioned type, in which there are avoided the stresses on the light conductor which are caused through exposure to sterilizing or through cleaning.

The advantages which are attained through the present invention can be essentially ascertained in that the light conductor is protected against thermal stresses through the intermediary of a special surface coating, as a result of which there is prevented any deterioration in the discharge or exit of light from the end surfaces of the light conductor.

BRIEF DESCRIPTION OF THE DRAWINGS

Reference may now be had to the following detailed description of exemplary embodiments of light conductors pursuant to the invention, taken in conjunction with the accompanying drawings; in which.

DETAILED DESCRIPTION

Figure 1:
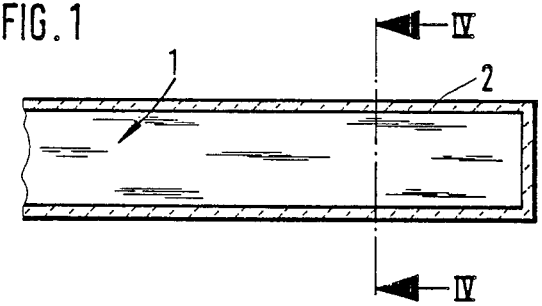
FIG. 1 illustrates a longitudinal sectional view of the end region of a light conductor which is constituted from a solid material.
Figure 2:
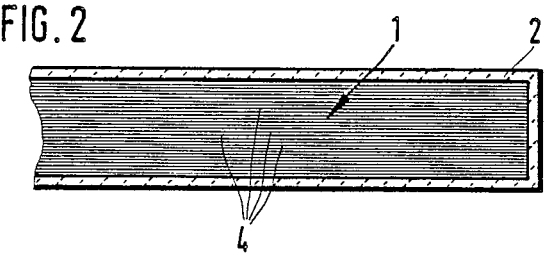
FIG. 2 illustrates a longitudinal section of the end region of a light conductor which is constituted from a fibrous material.
Figure 3:
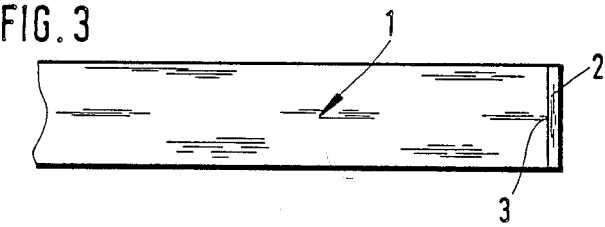
FIG. 3 illustrates a further embodiment of the invention, modified with respect to the light conductor of FIG. 1.
Figure 4:
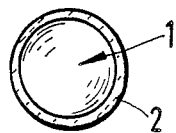
FIG. 4 illustrates a sectional view taken along line IV—IV in FIG. 1.

In the exemplary embodiments of FIGS. 1, 3 and 4, the light conductor 1 is constituted from a solid material. In the embodiment pursuant to FIG. 2, the light conductor 1 is formed from a fibrous material. The indicated fibers in FIG. 2 are identified by the reference numeral 4. For example, the material may be constituted of either glass or plastic. The illustrated light conductor 1 can be flexible or rigid in structure.

The rod-shaped light conductor 1 which is employable for medical purposes possesses a surface coating 2 which is constituted of a heatproof or temperature-resistant transparent or light-transmissive material. In order to avoid damaging of the surface coating 2 due to the rough operation encountered in washing machines or the like, the light-transmissive material which forms the surface coating for the light conductor is not only heatproof or temperature-resistant, but is also robust or of high mechanical strength. In order to avoid any damage caused by corrosive media, for example, sterilizing or disinfecting media, the light-transmissive material which forms the surface coating 2 is not only temperature-resistant, and when necessary of a high mechanical strength, but is also impervious to chemicals.

The surface coating 2 can be constituted of a quartz coating and/or an aluminum oxide coating. Furthermore, the surface coating 2 can be constituted of a coating which is applied under a high vacuum and/or by means of a plasma-jet spraying process.

Expediently, pursuant to FIGS. 1 and 2 of the drawings, the entire rod-shaped light conductor 1; in essence, the circumferential surface thereof and the end surfaces 3, are provided with the surface coating 2. However, quite frequently it is also sufficient that, as shown in FIG. 3, the surface coating 2 is only provided on the end surfaces 3 of the light conductor 1. Preferably, the end surfaces 3 of the light conductor 1 are polished, which for example, is constituted of optical glass.

With respect to the surface coating 2, the light conductor 1 can possess any suitable shape, for example, an oval cross-sectional configuration. Expediently, however, the light conductor 1 possesses a round cross-sectional configuration in accordance with FIG. 4.

What is claimed is:

1. A medical instrument having a rod-shaped light conductor for conducting light for illumination purposes, wherein the end surface of the rod-shaped light conductor is polished, and said light conductor possesses a surface coating constituted of a quartz coating applied only to the polished end surface of the light conductor by a high vacuum process to provide a heat-resistant, light-transmissive coating of high mechanical strength which is resistant to chemical corrosion.

2. A light conductor as claimed in claim 1, wherein the surface coating is applied by a plasma-jet spraying process.

3. A medical instrument having a rod-shaped light conductor for conducting light for illumination purposes, wherein the end surface of the rod-shaped light conductor is polished, and said light conductor possesses a surface coating constituted of an aluminum oxide coating applied only to the polished end surface of the light conductor by a high vacuum process to provide a heat-resistant, light-transmissive coating of high mechanical strength which is resistant to chemical corrosion.

4. A light conductor as claimed in claim 3, wherein the surface coating is applied by a plasma-jet spraying process.